(12) United States Patent
Blomlöf et al.

(10) Patent No.: US 6,340,455 B1
(45) Date of Patent: Jan. 22, 2002

(54) TESTKIT AND METHOD

(75) Inventors: Leif Blomlöf, Lindingö ; Sven Lindskog, Stockholm; Olle Zetterström, Järfälla, all of (SE)

(73) Assignee: Peridoc AB, Stockholm (SE)

( * ) Notice: Subject to any disclaimer, the term of this patent is extended or adjusted under 35 U.S.C. 154(b) by 0 days.

(21) Appl. No.: 09/308,365

(22) PCT Filed: Nov. 20, 1997

(86) PCT No.: PCT/SE97/01949

§ 371 Date: Jun. 23, 1999

§ 102(e) Date: Jun. 23, 1999

(87) PCT Pub. No.: WO98/22147

PCT Pub. Date: May 28, 1998

(30) Foreign Application Priority Data

Nov. 22, 1996 (SE) ................................................. 9604302

(51) Int. Cl.[7] ........................... A61B 10/00; A61K 39/02
(52) U.S. Cl. ................ 424/9.81; 424/282.1; 424/234.1; 424/9.8; 435/7.1; 435/7.24; 435/7.32; 435/7.4; 435/970; 435/971; 435/975; 514/900; 514/901; 514/902
(58) Field of Search ............................ 424/9.81, 282.1, 424/234.1; 435/7.1, 7.32, 7.24, 7.4, 970, 971, 975; 514/900, 901, 902

(56) References Cited

U.S. PATENT DOCUMENTS

| | | | |
|---|---|---|---|
| 4,812,402 A | * | 3/1989 | Nilsson |
| 5,366,733 A | * | 11/1994 | Brizzolara et al. .......... 424/426 |
| 5,712,102 A | * | 1/1998 | Darveau .................... 435/7.32 |
| 6,129,917 A | * | 11/2000 | Potempa et al. ......... 424/184.1 |

FOREIGN PATENT DOCUMENTS

DE 4041351 7/1992

OTHER PUBLICATIONS

"The Role of Systemic Conditions and Disorders in Periodontal Disease" Robert J. Genco et al., *Periodontology 2000*, vol. 2 (1993) pp. 98–116.

"Successive Removal of Periodontal Tissues: Marginal Healing Without Plaque Control" S. Lindskog et al., *J. Clin Periodontal*, vol. 20 (1993) pp. 14–19.

"New Concepts of Destructive Periodontal Disease" S.S. Socransky et al., *Journal of Clinical Periodontology*, vol. 11 (1984) pp. 21–32.

Ginanni et al. Ann Allergy 1991; 66: 39–42, 1991.*

* cited by examiner

*Primary Examiner*—Diana Dudash
*Assistant Examiner*—Shahnam Sharareh
(74) *Attorney, Agent, or Firm*—Burns, Doane, Swecker & Mathis, L.L.P.

(57) ABSTRACT

Skin prick test for the determination of the predisposition of an individual to develop marginal periodontitis, said kit comprising: (a) a first reagent containing a known quantity of a surface structure common to anaerobic Gram negative pathogens which is capable of triggering the inflammatory response associated with periodontitis and gingivitis; (b) second reagent containing an agonist to said individual; (c) a negative control; and (d) instructions for the use of said kit; and a method for such determination of predisposition.

1 Claim, No Drawings

TESTKIT AND METHOD

The present invention relates to a skin prick test kit for the determination of the predisposition of an individual to develop marginal periodontitis. The invention also involves a method for the determination of such predisposition.

BACKGROUND OF THE INVENTION

The most frequent disease that affects the attachment apparatus of the teeth or the periodontium is gingivitis. It is caused by our indigenous bacterial flora and is, for some individuals a first step towards marginal periodontitis. A shift towards more anaerobic bacteria in the bacterial plaque is thought to be the reason why gingivitis turns into marginal periodontitis. Despite the fact that almost all individuals suffer from gingivitis, there is no clear relation between the degree of gingivitis and development of marginal periodontitis. Epidemiological studies have, however, shown that between 5 and 10% of the adult population develop severe marginal periodontitis, while a moderate form affects 50 to 80%.

Progression of periodontitis is influenced by a multitude of modifying factors (Genco, RJ, Löe H. The role of systemic conditions and disorders in periodontal disease. Periodontol 2000 1994; 2: 98–116). These can be divided into systemic factors which affect the entire dentition and local factors which affect a single tooth or tooth surface.

The teeth are attached to the alveolar bone through their roots. A thin layer of mineralized cementum is found along the surface of the roots. The cementum layer anchors collagen fibers which extend to the adjacent alveolar bone. The space, thus created between the root and the bone surfaces, is occupied mainly by collagen fibers and connective tissue cells (fibroblasts). The soft tissue, known as the periodontal membrane or ligament, is a highly specialized connective tissue. It has the capacity to form bone as well as cementum and can, provided the right conditions are given, form a new attachment apparatus in areas of the root where it has been lost to periodontal disease (Lindskog S, Lengheden A, Blomlöf L. Successive removal of periodontal tissues. Marginal healing without plaque control. J. Clin. Periodontol 1993; 20: 14–9).

Periodontal disease is, second to tooth decay, the most frequent oral disease. It is a progressive disease and affects, in its severe form, 5 to 10% of the population in industrialized countries, leading to partial or complete tooth loss. However, most adults have one or more teeth affected by the disease. The disease is, in its most common form known as marginal periodontitis. It is caused by accumulation of bacterial deposits on tooth surfaces along the gingival margins. These bacteria, predominantly anaerobic originate from the hosts indigenous oral microflora and elicit an inflammatory reaction in the gingiva which results in destruction of tooth-supporting tissues (periodontal membrane and alveolar bone). The destruction of tooth-supporting tissues results in a deepening of the space (periodontal pocket) between the root of the tooth and the gingiva. The disease progresses as bacteria migrate apically into the periodontal pocket, which deepens more and more as a result of the soft tissue inflammation. Unless adequate treatment is instigated, the tooth becomes mobile and will eventually fall out when enough tooth-supporting tissues have been destroyed.

Three theories on or models for progression of marginal periodontitis have been proposed (Socransky SS, Haffajee AD, Goodson J, Lindhe J. New concepts of destructive periodontal disease. J. Clin Periodontol 1984; 11: 21–32):

1. A slow continuous loss of attachment throughout life.
2. Random periods of attachment loss throughout life.
3. Localized attachment loss during certain periods in life.

There is reason to believe that all three theories are valid, each within a certain subpopulation of patients suffering from marginal periodontitis. The first theory/model applies to the majority of patients, 50 to 80% of the population, which show a moderate form of marginal periodontitis. The third theory/model applies to juvenile periodontitis which affects young patients and then most often only the first permanent molars. The second theory/model accounts for the 5 to 10% of the population which suffer from severe marginal periodontitis.

Within the group of patients suffering from severe marginal periodontitis and which lose periodontal attachment during random periods throughout life (theory/model 2 above) a large number of patients fail to respond to treatment (refractory patients). These patients have most probably a "multi-factorial genetic predisposition" to develop severe marginal periodontitis.

This genetic predisposition has been suggested to lead to an inflammatory overreaction to marginal bacterial plaque which in turn causes destruction of the marginal periodontium.

SUMMARY OF THE INVENTION

The main object of the present invention is to provide new techniques residing in a screening test to identify within a given population individuals who have predisposition to develop marginal periodontitis.

Another object of the present invention is to provide a skin prick test kit for such determination of predisposed individuals.

Another object of the invention is to provide a method for the determination of such predisposition of individuals within a given population.

For these and other objects which will be clear from the following disclosure the invention provides for a skin prick test kit for the determination of the predisposition of an individual to develop marginal periodontitis, said kit comprising:

a) a first reagent containing a known quantity of a surface structure common to anaerobic Gram negative pathogens which is capable of triggering the inflammatory response associated with periodontitis and gingivitis;

b) a second reagent containing an agonist to said individual;

c) a negative control; and d) instructions for the use of said kit.

It is preferred that said first reagent contains a structure selected from the non-polysaccharide entity of surface lipo- or proteoconjugates of such anaerobic Gram negative pathogens.

It is particularly preferred that said conjugate is a lipopolysaccharide, and in such conjugate it is particularly preferred that said entity is Lipid A or an equivalent thereof of same biological function.

In regard to the second reagent said agonist can be any substance capable of producing an inflammatory response on challenge of an individual subject to test. Although any agonist of such function can be used it is preferably selected from histamine, serotonin, prostaglandins, leukotrienes and bradykinin.

It is particularly preferred to use as an agonist histamine which is a conventional challenge substance used in testing immunologic reaction.

The invention also provides for a method for the determination of the predisposition of an individual to develop marginal periodontitis. In such a method the skin prick test is performed by challenging an individual subject to testing with a first reagent as defined above, evaluating the reaction of said challenge. In this method lack of reaction or generation of only a minor reaction indicates predisposition to develop a marginal periodontitis.

As will be shown below by experimental data patients refractory to treatment surprisingly present a reverse response, i.e. they do not respond as readily as healthy individuals with an inflammatory reaction to a given common Gram negative bacterial antigen, such as Lipid A. This impaired response could therefore lead to an unimpaired or uncontrolled growth of the marginal microflora, especially the anaerobic subgingival pathogens which, when they reach a critical volume, initiate a period of marginal attachment loss. The techniques presented by the present invention residing in the administration of a suitable antigen, such as Lipid A, thus has the potential of serving as a screening test for the early identification of individuals which have a predisposition to develop severe marginal periodontitis.

In regard to the first reagent any antigen or surface structure common to Gram negative bacterial periodontitis pathogens can be used in the test method according to the present invention. Such antigens are frequently part of surface conjugates of said pathogens, such as lipo- or proteopolysaccharides. Since the polysaccharide part of such conjugates has a structure varying with the type of bacterial strain involved, it is preferred to use the non-polysaccharide entity of such conjugates, said entity being unaltered regardless of bacterial strain.

With regard to the second reagent used in the present invention to confirm a positive reaction, it goes without saying that any agonist can be used for such purpose.

the polysaccharide part of LPS, it remains unaltered regardless of bacterial strain. LPS triggers a number of biological activities most notably the inflammatory response in periodontitis and gingivitis.

Skin Prick Test with Lipid A was performed on three groups of individuals:

Patients with severe marginal periodontitis which does not respond to treatment (refractory patients).

Patients with severe marginal periodontitis which responds to treatment.

Healthy control individuals without marginal periodontitis.

(The test was performed according to a routine procedure as described in Aas K, Backman A, Berlin L, Weeke B. Standardization of allergen extracts with appropriate methods. The combined use of skin prick testing and standardization of allergen extracts. Acta Allergol 1978; 33:238–240, and in Malling H–J. The skin prick testing and the use of histamine references. Allergy 1984; 39:596–601).

Patient and disease characteristics for the three groups can be found in Table 1 below. GI (gingival index) was used as measure of active disease. Refractory patients all had a GI>20. The test substance was Lipid A dissolved in water (0.1 mg/ml and 1 mg/ml). Histamine (10 mg/ml in water) and water served as positive and negative controls, respectively. The result was registered after 18 to 24 hours.

TABLE 1 Patient and disease characteristics for the two test groups and the control group. No significant differences were found between the groups with marginal periodontitis with respect to gender, age, pocket depth and number of teeth.

| Test/control group | n | % female % male | Mean age | No. of teeth | Marginal bone loss | Mean periodontal pocket depth | Mean gingival index |
|---|---|---|---|---|---|---|---|
| Patients with severe marginal periodontitis which does not respond to treatment (GI > 20) | 14 | 42.9 57.1 | 45.7 | 21.1 | 32.8% | 3.2 | 29.2 |
| Patients with severe marginal periodontitis which responds to treatment (GI ≤ 20) | 38 | 44.7 55.3 | 45.4 | 21.3 | 30.3% | 2.9 | 11.1 |
| Healthy control individuals without marginal periodontitis | 16 | 81.2 18.8 | 42.1 | — | 1.8 mm | — | — |

Furthermore, the negative control for confirming negative reaction can be simply constituted by pyrogene free water.

DETAILED DESCRIPTION OF THE INVENTION

The present invention will be further illustrated by specific experimental data, but it is to be noted that the invention is not restricted to the experiments presented below since alterations and modifications will be obvious to the skilled artisan upon reading of the disclosure.

EXAMPLE

Skin Prick Test Using Lipid A

Lipid A is a unique part of endotoxins, lipopolysaccharides (LPS) produced by all periodontitis pathogens. Unlike All individuals reacted positively to histamine and negatively to the vehicle (water). Students t-test was employed to test levels of significance for differences between test and control groups.

Results from the Skin Prick Test can be found in Table 2 below.

TABLE 2 Skin Prick Test with Lipid A performed on three groups of individuals: patients with severe marginal periodontitis which does not respond to treatment (refractory patients), patients with severe marginal periodontitis which responds to treatment and healthy control individuals without marginal periodontitis.

| Test/control group | n | % + with 1 mg Lipid A | P | % + with 0.1 mg Lipid A | P |
|---|---|---|---|---|---|
| Patients with severe marginal periodontitis which does not respond to treatment (GI > 20) | 14 | 7.1 | 0.0007↓ ↓ 0.0093↓ ↓ | 7.1 | ns↓↓ ns↓ |
| Patients with severe marginal periodontitis which responds to treatment (GI ≤ 20) | 38 | 57.9 | ns↓ | 21.1 | ns↓ |
| Healthy control individuals without marginal periodontitis | 16 | 50.0 | | 18.8 | |

Patients with severe marginal periodontitis not responding to treatment (refractory patients) showed almost no positive response to Lipid A which was significantly different from the results from patients with severe marginal periodontitis which responds to treatment and healthy control individuals without marginal periodontitis. Refractory patients also required higher concentrations of Lipid A to respond. Although the invention is not restricted to any particular theory, this can be interpreted as an impaired inflammatory reactivity to periodontitis pathogens in refractory patients and the test can be used to screen individuals to identify those susceptible to severe refractory periodontitis before periodontitis has progressed too far. Thus, preventive measures could be specifically directed towards these patients.

What is claimed is:

1. A method for determination of predisposition of an individual to develop marginal periodontitis comprising:
   a) performing a screening test on said individual with a first reagent comprising a surface structure common to anaerobic Gram negative pathogens to elicit a reaction in the individual, wherein the first reagent is capable of triggering an inflammatory response associated with periodontitis and gingivitis in the individual; and
   b) evaluating the reaction, lack of reaction or minor reaction of the individual to the first reagent of the screening test, indicating the predisposition of the individual to develop marginal periodontitis;
   wherein step a) is accompanied by challenge with a negative control to confirm negative reaction;
   wherein said first reagent comprises a structure selected from a non-carbohydrate entity of surface lipo- or proteoconjugates of said pathogens, wherein a second reagent is an agonist capable of producing an inflammatory response on challenge of said individual to confirm positive reaction selected from histamine, serotonin, prostaglandins, leukotrienes and bradykinin, and wherein said negative control is pyrogene free water; and
   wherein said first reagent comprises Lipid A in a concentration within the range about 0.05 to about 2 mg/ml.

* * * * *